US012240980B2

(12) United States Patent
Modha et al.

(10) Patent No.: US 12,240,980 B2
(45) Date of Patent: Mar. 4, 2025

(54) SOFTER BLENDED NITRILE ELASTOMERIC ARTICLE

(71) Applicant: O&M Halyard, Inc., Mechanicsville, VA (US)

(72) Inventors: Shantilal H. Modha, Milton, GA (US); Sopha Issara, Songkhala (TH); Siew Hoe Tan, Penang (MY)

(73) Assignee: O&M Halyard, Inc., Mechanicsville, VA (US)

( * ) Notice: Subject to any disclaimer, the term of this patent is extended or adjusted under 35 U.S.C. 154(b) by 178 days.

(21) Appl. No.: 17/511,649

(22) Filed: Oct. 27, 2021

(65) Prior Publication Data

US 2022/0135776 A1   May 5, 2022

Related U.S. Application Data

(60) Provisional application No. 63/107,177, filed on Oct. 29, 2020.

(51) Int. Cl.
| | | |
|---|---|---|
| *C08L 9/04* | (2006.01) | |
| *A41D 19/00* | (2006.01) | |
| *A41D 19/04* | (2006.01) | |
| *A41D 31/18* | (2019.01) | |
| *A61B 42/10* | (2016.01) | |
| *B29C 33/58* | (2006.01) | |

(Continued)

(52) U.S. Cl.
CPC ............ *C08L 9/04* (2013.01); *A41D 19/0062* (2013.01); *A41D 19/04* (2013.01); *A41D 31/18* (2019.02); *A61B 42/10* (2016.02); *B29C 33/58* (2013.01); *B29C 41/003* (2013.01); *B29C 41/14* (2013.01); *C08J 5/02* (2013.01); *C08J 7/126* (2013.01); *B29K 2105/0064* (2013.01); *B29L 2031/4864* (2013.01); *C08J 2309/04* (2013.01); *C08J 2411/02* (2013.01); *C08L 2201/52* (2013.01); *C08L 2312/00* (2013.01)

(58) Field of Classification Search
CPC .... C08L 9/04; C08L 2201/52; C08L 2312/00; A41D 19/0062; A41D 19/04; A41D 31/18; B29C 33/58; B29C 41/003; B29C 41/14; C08J 5/02; C08J 7/126; C08J 2309/04; C08J 2411/02; B29K 2105/0064; B29L 2031/4864
See application file for complete search history.

(56) References Cited

U.S. PATENT DOCUMENTS

| | | |
|---|---|---|
| 6,706,816 B2 | 3/2004 | Williams et al. |
| 10,344,158 B2 | 7/2019 | Foo et al. |

(Continued)

FOREIGN PATENT DOCUMENTS

| | | |
|---|---|---|
| WO | WO 01/90236 A1 | 11/2001 |
| WO | WO 2011/068394 A1 | 6/2011 |

OTHER PUBLICATIONS

International Search Report and Written Opinion for PCT/US2021/056750, dated Feb. 24, 2022, 14 pages.

*Primary Examiner* — Michael C Miggins
(74) *Attorney, Agent, or Firm* — Dority & Manning, P.A.

(57) ABSTRACT

An elastomeric article is formed from a blend of nitrile rubber and polychloroprene rubber. The elastomeric article can be a glove, such as a medical exam glove. The elastomeric article is softer than a conventional nitrile elastomeric article. The elastomeric article is formed from a blended rubber latex emulsion of nitrile and polychloroprene. The blended rubber latex emulsion may be free of sulfur and vulcanization accelerators.

11 Claims, 2 Drawing Sheets

(51) Int. Cl.
  *B29C 41/00*  (2006.01)
  *B29C 41/14*  (2006.01)
  *B29K 105/00*  (2006.01)
  *B29L 31/48*  (2006.01)
  *C08J 5/02*  (2006.01)
  *C08J 7/12*  (2006.01)

(56) References Cited

U.S. PATENT DOCUMENTS

| | | |
|---|---|---|
| 10,626,283 B2 | 4/2020 | Mercado et al. |
| 2003/0017286 A1 | 1/2003 | Williams et al. |
| 2015/0135403 A1 | 5/2015 | Mercado et al. |
| 2016/0194494 A1 | 7/2016 | Foo et al. |

SOFTER BLENDED NITRILE ELASTOMERIC ARTICLE

RELATED APPLICATIONS

The present application claims priority to U.S. Provisional Application Ser. No. 63/107,177, filed on Oct. 29, 2020, which is incorporated herein in its entirety by reference thereto.

FIELD OF THE INVENTION

The subject matter of the present invention relates generally to a softer nitrile elastomeric article formed from a blend of nitrile rubber and chloroprene rubber.

BACKGROUND

The development of modern synthetic rubber materials has made possible the manufacture of a wide range of dipped elastomeric articles, such as gloves, balloons, and condoms, having varying properties of strength and chemical resistance. Gloves are used as an infection protection device to protect the wearer from exposure to bacteria, viruses, pathogens, infections, diseases, etc. that could transfer from a surface or bodily fluid (e.g., blood) to the wearer's skin. Gloves are also used in manufacturing environments to prevent the wearer from coming into contact with various chemicals, and in some medical settings, gloves can be used to protect the wearer from certain pharmaceuticals that may be toxic, such as chemotherapy drugs.

Conventional medical exam gloves are formed from materials such as nitrile rubber, polyvinyl chloride, and natural rubber latex, each of which have their own shortcomings. Glove consumers have been moving away from natural rubber gloves due, in part, to an increasing rate of significant allergic reactions to proteins in natural rubber latex among health professionals as well as the general population. The industry has increasingly moved to latex emulsions based on synthetic rubber materials. While hospitals, laboratories, or other work environments that use rubber gloves often want to go "latex free" to better protect their workers, the higher cost of non-latex products, such as nitrile rubber, often limits their ability to make the change. For example, nitrile rubber gloves may cost two or more times the price of the natural rubber latex or vinyl-based counterparts. Elastomeric articles formed from nitrile rubber require a number of crosslinkers and accelerators, which can add to the cost of manufacturing the nitrile articles. In addition to being more expensive, nitrile-butadiene rubber medical exam gloves are typically stiffer and are perceived as much less comfortable to wear in comparison to similar gloves made from natural rubber latex materials. Although comparatively inexpensive, polyvinyl chloride medical exam gloves have a number of shortcomings, including being relatively inelastic, having relatively low tensile strength, having relatively greater amounts of pinhole defects; and leaching certain toxic components. These shortcomings can result in less comfort for the wearer, a weaker glove with higher permeability or poorer barrier protection against some common chemicals, and harm to the user and/or environment. In view of these and other factors, consumers continue to seek an alternative to existing conventional gloves.

Consequently, there is a need for elastomeric articles such as gloves that meets the requirements for medical gloves while reducing cost compared to conventional gloves. In particular, elastomeric gloves having improved softness and comfort for a user would also be useful.

SUMMARY

Objects and advantages of the invention will be set forth in part in the following description, or may be obvious from the description, or may be learned through practice of the invention.

The present invention is directed to an elastomeric article. The article includes a flexible layer of elastomeric material. The elastomeric material is formed from a blended emulsion of nitrile rubber and chloroprene rubber. The article has a first surface and a second surface.

In one particular embodiment, the article may be a glove. Moreover, the first surface may be a donning side of the glove and the second surface may be a grip side of the glove.

In another embodiment, the ratio of nitrile rubber to chloroprene rubber in the blended emulsion can be in a range from about 50:50 to about 95:5.

In an additional embodiment, the blended emulsion may include a solids content of between about 15 percent and about 30 percent, by weight.

In a further embodiment, coagulation of the blended emulsion to form the elastomeric article may be accelerated by a metallic salt, wherein the metallic salt includes nitrate, sulfate, or chloride salts of calcium, aluminum, or zinc, or a combination thereof. Moreover, coagulation of the blended emulsion to form the elastomeric article may be further accelerated by a crosslinker, wherein the crosslinker is a trivalent compound. Further, the metallic salt may be a divalent compound. For instance, the metallic salt may be zinc oxide. Moreover, the trivalent compound crosslinker may be a metallic oxide that forms bonds with carboxyl groups of the nitrile rubber.

In another embodiment, coagulation of the blended emulsion to form the elastomeric article may be accelerated by a crosslinker, wherein the crosslinker is a trivalent compound. Moreover, the trivalent compound crosslinker may be a metallic oxide that forms bonds with carboxyl groups of the nitrile rubber.

In one more embodiment, the blended emulsion may be free from sulfur.

In a further embodiment, the blended emulsion may be free from a dithiocarbamate accelerator, zincediethyldithiocarbamate (ZDEC), zinc mercaptobenzothiazole (ZMBT), diphenyl guanidine (DPG), or a combination thereof.

The present invention is further directed to a process for making an elastomeric article. The process includes steps of:
 coating a surface of a mold with a coagulant solution and a release agent;
 partially drying the mold coated with the coagulant solution and release agent;
 immersing the partially dried mold into a blended rubber latex emulsion comprising nitrile-butadiene latex and polychloroprene to form a coagulated layer of nitrile-butadiene rubber latex and polychloroprene rubber on the mold surface;
 removing the mold from the blended emulsion;
 immersing the mold containing the coagulated layer of nitrile-butadiene rubber latex and polychloroprene rubber into an aqueous bath and then drying the coagulated blend of nitrile-butadiene rubber latex and polychloroprene to form an elastomeric article on the mold;
 immersing the mold containing the elastomeric article into a chlorinating bath to chlorinate an exterior surface of the elastomeric article on the mold; and removing the elastomeric article from the mold by inverting the elastomeric article such that the chlorinated exterior surface of the glove body forms an interior surface of the elastomeric article.

In one particular embodiment of the process, the blended emulsion may have a total latex solids content of between about 15 percent and about 30 percent, by weight.

In another embodiment, the blended emulsion may have a ratio of nitrile rubber to polychloroprene rubber in a range from about 50:50 to about 95:5.

In an additional embodiment, coagulation of the blended emulsion to form the elastomeric article may be further accelerated by a crosslinker, wherein the crosslinker is a trivalent compound.

In yet another embodiment, the trivalent compound crosslinker may be a metallic oxide that forms bonds with carboxyl groups of the nitrile rubber.

In one more embodiment, the blended emulsion may be free from a dithiocarbamate accelerator, zincediethyldithiocarbamate (ZDEC), zinc mercaptobenzothiazole (ZMBT), diphenyl guanidine (DPG), or a combination thereof.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
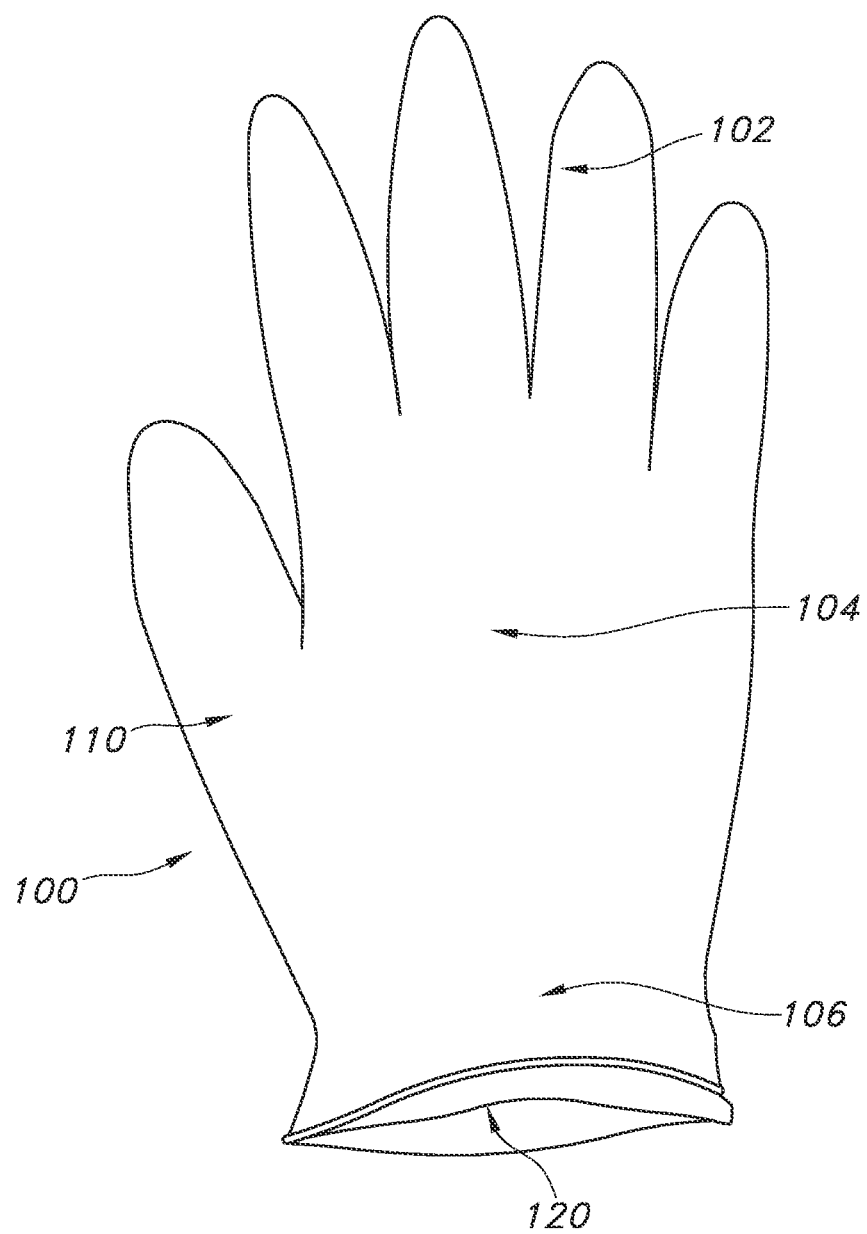
FIG. 1 illustrates a perspective view of an elastomeric article in the form of a glove according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

A desirable attribute for elastomeric articles that are worn on the body is softness or pliability of the polymeric material. The present invention describes the creation of elastic articles, such as gloves, made from a nitrile polymer formulation. As used herein, the terms "elastic" or "elastomeric" generally refer to a material that, upon application of a force, is stretchable to an extended, biased length. Upon release of the stretching, biasing force, the material will substantially recover to near net shape or original dimensions.

Generally speaking, the present invention is directed to an elastomeric article formed from a blend of nitrile rubber and polychloroprene rubber. The elastomeric article can be a glove, such as a medical exam glove. The elastomeric article is softer than a conventional nitrile elastomeric article. The elastomeric article is formed from a blended rubber latex emulsion of nitrile and polychloroprene. The blended rubber latex emulsion may be free of sulfur and vulcanization accelerators. The present invention is further directed to a method of forming an elastomeric article formed from a blended emulsion of nitrile rubber and polychloroprene, in which the blended rubber latex emulsion may be free of sulfur and vulcanization accelerators. The present inventors have found that the blend of nitrile rubber and polychloroprene of the present invention does not require the addition of sulfur and/or vulcanization accelerators as nitrile elastomeric articles conventionally require. The specific features of the elastomeric article and method of the present invention may be better understood with reference to FIGS. 1-2.

Referring now to FIG. 1, one embodiment of a softer elastomeric article of the present invention in the form of a glove 100 is shown. The glove 100 is made from an elastomeric substrate and includes a finger region 102, a palm region 104, and a forearm or cuff region 106. The glove 100 has an inner donning surface 120 and an outer grip surface 110. The inner donning surface 120 is configured to contact the wearer's skin and is made to be soft, smooth and silky to reduce friction when donning the glove 100 on the wearer's hand. The outer grip surface 110 of the glove 100 of the present invention is configured to be exposed away from the wearer and typically has an enhanced gripping texture compared to the donning surface 120. However, the grip surface 110 can be made sufficiently smooth through a friction treatment (described in detail below) to reduce friction. The cuff region 106 of the glove 100 may extend beyond the wearer's wrist and over a portion of the wearer's forearm. The glove 100 may have a total average length L from the finger region to the cuff region of about 200 mm to about 400 mm (about 8 to about 16 inches), such as from about 250 mm to about 355 mm (about 10 to about 14 inches), for example about 310 mm (about 12 inches). The extended length of the glove may provide additional coverage to a wearer. For example a healthcare professional handling chemotherapy drugs may employ the extended length of the cuff 106 of the glove 100 under a cuff of a chemotherapy gown for additional coverage.

Using the protocol described in ASTM D3767, procedure A, glove thicknesses are measured by taking an elastomeric substrate portion from an exemplary glove 100. The elastomeric substrate can have an average thickness ranging from about 0.03 mm to about 0.15 mm, for example from about 0.05 mm to about 0.12 mm. When made into a glove 100, according to certain embodiments, the substrate can have a thickness in the palm region of about 0.05 mm to about 0.11 mm. More desirably, the substrate can have a thickness in the palm region ranging from about 0.06 mm to about 0.08 mm, for example about 0.07 mm. The glove 100 may have a thickness in the middle finger region ranging from about 0.08 mm to about 0.16 mm, for example about 0.10 mm. The glove 100 may have a thickness in the cuff region 106 ranging from about 0.04 mm to about 0.10 mm, for example about 0.06 mm.

The gloves made using the current invention are softer, less bulky and more pliable to wear, providing greater comfort compared to conventional nitrile rubber gloves. With a softer material, the wearer also enjoys greater comfort and tactile sensation in the hand and fingertips than compared with regular gloves.

Furthermore, after aging at 70° C.+/−2° C. for 168 hours+/−2 hours, a glove 100 made according to the present invention with a thickness of about 0.06-0.09 mm in the palm area may have a tensile strength ranging from about 25 MPa to about 35 MPa, for example about 31 MPa. Further, the aged glove can have an ultimate elongation at break ranging from about 450% to about 650%, such as from about 550% to about 625%, for example about 575%.

The precise point of measurement in order to determine that data described above is that defined in American Society for Testing and Materials (ASTM) test standard D-412-98a (Reapproved 2002), "Standard Test Methods for Vulcanized Rubber and Thermoplastic Elastomers—Tension, published January 2003, the contents of which are incorporated herein by reference. These test methods cover procedures used to evaluate the tensile (tension) properties of vulcanized thermoset rubbers and thermoplastic elastomers. The determination of tensile properties starts with test pieces taken from a sample material and includes the preparation of specimens and the testing of the specimens. Specimens may be in the shape of dumbbells, rings, or straight pieces of uniform cross-sectional area. Measurements of tensile stress, tensile stress at a given elongation, tensile strength, yield point, and ultimate elongation are made on specimens that have not been pre-stressed. Tensile stress, tensile strength, and yield point are based on the original cross-sectional area of a uniform cross-section of the specimen.

Various glove layer components, glove formation procedures, and several examples contemplated by the present invention are discussed in more detail below.

Nitrile Rubber Formulation

The elastomeric article or glove of the present invention may generally be formed from a blend of elastomeric materials to form a softer elastomeric material than conventional nitrile gloves. In particular, the blend of elastomeric materials includes nitrile rubbers (e.g., acrylonitrile butadiene) and chloroprene rubbers.

Nitrile-butadiene rubber (commonly referred to as "nitrile rubber" or "NBR") is a family of amorphous unsaturated copolymers of acrylonitrile and various butadiene monomers (1,2-butadiene and 1,3-butadiene). This form of synthetic rubber is generally resistant to aliphatic hydrocarbons, such as fatty tissue, oils, and other chemicals. Nitrile rubber has been used to create molded goods, footwear, adhesives, sealants, sponge, expanded foams, and floor mats. Its resilience makes conventional nitrile rubber a good material for disposable gloves used in laboratory, cleaning, industrial work, and clinical situations. Conventional medical exam gloves made from conventional nitrile rubber generally are three times more puncture-resistant than conventional medical exam gloves made from natural rubber (i.e., formed from natural rubber latex) or polyvinyl chloride.

Polychloroprene rubber (commonly referred to as "neoprene") is a family of synthetic rubbers that are produced by polymerization of chloroprene (2-chloro-1,3-butadiene). This form of rubber is generally resistant to heat and hydrocarbon oils, and is more resistant to degradation than natural rubber and most other synthetic rubbers. Polychloroprene rubber has been used to create molded goods, protective apparel, industrial applications, protective packaging (e.g., laptop sleeves), sealants, expanded foams, insulation for sound, electrical and/or fire resistance, and many other uses. Gloves made from polychloroprene rubber generally provide improved resistance to extreme temperature and toxic and hazardous chemicals as compared to other conventional medical exam gloves.

As a disposable product, a rubber glove made according to the present invention will have a mass that is at least about 40-50% less than a typical polyvinyl chloride-based glove of the same type (e.g., medical exam, household, or industrial) and size (i.e., small, medium, large, x-large). For example, a rubber medical exam glove according to the present invention that is made to the conventional size "M" or "Medium" will have a mass that is at least about 40 percent to about 50 percent less (or an even greater percentage less) than a typical polyvinyl chloride medical exam glove that is made to the conventional size "M" or "Medium". In particular, a rubber glove made according to the present invention may have a mass based on size as follows: about 3.05 grams for a size "Extra-Small" or "XS"; about 3.40 grams for a size "Small" or "S"; about 3.70 grams for a size "Medium" or "M"; about 4.40 grams for a size "Large" or "L"; about 5.20 grams for a size "Extra-Large" or "XL". In contrast, a typical polyvinyl chloride-based glove of the same type may have a mass based on size as follows: about 4.70 grams for a size Small; about 5.20 grams for a size Medium; about 5.60 grams for a size Large; and about 6.50 grams for a size Extra-Large.

As previously noted, various published reports describing comparative testing of conventional polyvinyl chloride medical exam gloves and nitrile rubber medical exam gloves show that polyvinyl chloride medical exam gloves have a greater incidence of leakage. Given that vinyl is inherently a much weaker material in terms of tensile strength and is likely to have pinholes in the membrane, vinyl-based medical exam gloves require the use of a greater amount of material to achieve the same level of strength and integrity as a blended nitrile rubber and chloroprene rubber medical exam glove of the present invention. Thus, the blended nitrile rubber and chloroprene rubber medical exam gloves of the present invention contribute relatively less waste and have less environmental impact because they have substantially less mass than comparable polyvinyl chloride medical exam gloves.

From a commercial viewpoint, the blended nitrile rubber and chloroprene medical exam gloves of the present invention are cost competitive with inexpensive polyvinyl chloride medical exam gloves. That is, the blended nitrile rubber and chloroprene gloves of the present invention are more affordable than conventional nitrile rubber gloves as the cost of manufacturing the blended gloves of the present invention is reduced in comparison. The relatively lower cost of the blended nitrile rubber gloves of the present invention provides more opportunities for consumers to switch from conventional nitrile rubber gloves and polyvinyl chloride gloves to a better performing blended nitrile rubber glove (e.g., better stretch/tensile properties and enhanced softness/comfort) without much adverse economic impact in addition to avoiding exposure to hazardous components such as diethylhexylopthalate (DEHP) which can leach from polyvinyl chloride gloves.

The nitrile rubber that can be used in the latex blend to form the elastomeric article of the present invention can include a carboxylated nitrile that is compounded with various components based on 100 parts of the carboxylated nitrile/chloroprene blend ("phr" or parts per hundred rubber). The carboxylated nitrile rubber, chloroprene rubber and the various components compounded with the nitrile rubber and chloroprene rubber blend in the formulation of the present invention are discussed in more detail below.

Carboxylated nitrile, which is a terpolymer of butadiene, acrylonitrile, and organic acid monomers, has at least two properties that make it useful for manufacturing elastomeric articles. These two features are high strength and impermeability to certain hydrocarbon solvents and oils. Compounding and curing the rubber with other ingredients such as curing agents and activators is generally performed to optimize these properties. The level of each monomer in the polymer and the level of curing can affect the levels of strength and the chemical resistance in the finished article. Polymers with higher levels of acrylonitrile tend to have better resistance to aliphatic oils and solvents, but are also stiffer than polymers that have lower levels of acrylonitrile. While the chemical nature of the monomers from which the polymer is made offers some degree of chemical resistance, when the polymer molecules are chemically crosslinked, resistance to chemical swelling, permeation, and dissolution greatly increase.

The base polymer employed in the nitrile rubber can be a random terpolymer composition containing acrylonitrile, butadiene, and carboxylic acid components. It is believed that the particular advantageous properties of the present soft nitrile rubber materials can be due in part to the nature and interaction of a blend of acrylonitrile components in the composition. The blend can include two—a first and a second—acrylonitrile formulations in a compositional ratio ranging, respectively, from about 60:40 to 40:60. The orientation or placement of carboxyl groups on the nitrile polymer molecules—either outside or inside—can affect the reactivity of the carboxyl groups with zinc ions; hence, it is believed that some components exhibit softer, lower modulus properties and some components have good film forming properties.

The acrylonitrile content of the blended or combined terpolymer composition can range from about 17% by weight to about 45% by weight, such as from about 20% by weight to about 40% by weight, such as from about 20% by weight to about 35% by weight. In one embodiment, for instance, the acrylonitrile content can be between about 22% by weight and about 28% by weight, the methacrylic acid content can be less than about 10% by weight, and the remainder of the polymer can be butadiene. The methacrylic acid content should be less than about 15% by weight, preferably about 10% by weight, with butadiene making up the remainder balance of the polymer. The base terpolymer is made through a process of emulsion polymerization, and can be used while still in emulsion form to manufacture gloves or other elastomeric articles.

Further, the acrylonitrile polymer formulations that may be employed in the present invention can have a glass transition temperature (Tg) ranging from about −30° C. to about −10° C., such as from about −28° C. to about −12° C. In some embodiments, desirable nitrile polymer formulations, such as PolymerLatex X-1133 or Synthomer 6311 available from PolymerLatex GmbH, and Synthomer Ltd., respectively, can have a Tg between about −26° C. and about −18° C. Other nitrile formulations, such as Nantex® 635t, commercially available from Nantex Industry Co., Ltd. (Taiwan, R.O.C.), can have a Tg between about −25.5° C. to about −23.4° C. Another suitable nitrile polymer contemplated for use in the rubber blend of the elastomeric articles of the present invention is Lutex 105 manufactured by LG Chem, which has a Tg ranging from about −22° C. to about −14° C. and a total solids content of about 44.5% to about 45.5% and a pH of from about 8.0 to about 8.8.

It is believed, however, that the nitrile butadiene polymer properties do not come from components of the nitrile material, but from the structure of the polymer, which in turn, is determined by polymerization conditions. Polymer properties are very much affected by the polymer structure. Molecular structure of polymers can be very complex, with variability in molecular weight, molecular weight distribution, amount of branching, amount of crosslinking during polymerization, many possible types of chemical addition for diene monomers, etc. When several monomer types are combined into a polymer such as in a carboxylated acrylonitrile butadiene polymer used for glove manufacture, particularly when further blended with polychloroprene polymers, the structure becomes even more complex. Overall levels of each monomer type and the sequencing of the monomer units, in addition to the levels of polychloroprene polymer and the sequencing of the polychloroprene and the carboxylated acrylonitrile butadiene polymers, also contribute to the properties of the resulting polymer. When the repeating structure of the monomer units is random, such as in nitrile rubber used for elastomeric articles such as gloves, the physical properties of the polymer have increased influence from the polymer linearity (vs. branching) and molecular weight as compared to the properties of a homopolymer. This is because the properties expected from a regular repeating structure of a polymer made only from each single monomer change once that repeating structure is interrupted or otherwise altered by the addition of other types of monomer units. A high level of any particular monomer will likely increase the chance of contributing properties expected from a homopolymer made from that monomer, due to increased similarity of the repeating structures.

In carboxylated nitrile rubber used for thin glove manufacture, the acrylonitrile and carboxylic acid, which typically total approximately 35% by weight, add some plastic like character to the polymer with respect to resilience, permanent set, and stress relaxation. They also prevent a regular cis-1,4 repeating structure that would give polybutadiene its highest resilience and lowest set/relaxation. A general description of such a carboxylated nitrile rubber would be a long-chain random arrangement of its three component monomers, with branching and crosslinking. These branched, random terpolymers are formed into discrete tiny particles that are emulsified in water. In addition to the polymer structure, the particle structure also plays a part in the final properties of a glove. Parameters such as particle size, particle size distribution, level of particle agglomeration, particle density, etc., affect how the product is formed, and also its eventual properties. Although not required, the polymer structure can include a random terpolymer (as opposed to block or alternating terpolymer) of acrylonitrile, butadiene, and carboxylic acid. The properties depend on the average molecular weight, the molecular weight distribution, the linearity or degree of branching, the gel content (crosslinking during polymerization), and the microstructure (which monomer units are next to each other in short sections of the polymer chain).

Further, as described above, the elastomeric article of the present invention includes polychloroprene rubber blended with the nitrile rubber. The polychloroprene polymer is produced by free-radical polymerization of chloroprene. Polychloroprene resists degradation more than natural or synthetic rubbers, including having superior resistance to burning and heat. Moreover, polychloroprene has improved softness, flexibility and comfort as compared to conventional medical exam gloves, making polychloroprene a desirable material from a user's perspective. To form an elastomeric article, individual polymer strands of polychloroprene are crosslinked together, as will be described in further detail below. In some embodiments, desirable polychloroprene formulations include Chloroprene 750 liquid dispersion manufactured by Showa Denko, which has a solids content of about 50%, which exhibits good flex properties, excellent elasticity and extremely slow crystallization rate.

The nitrile and chloroprene can be provided in a blended latex emulsion. The blended rubber can be formed from about 5 parts to about 50 parts of chloroprene based on 100 parts of the nitrile/chloroprene blend ("phr" or parts per hundred rubber), and from about 50 parts to about 95 parts of nitrile based on 100 parts of the nitrile/chloroprene blend ("phr" or parts per hundred rubber). For instance, the blend can be formed from about 8 parts to about 20 parts of chloroprene based on 100 parts of the nitrile/chloroprene blend and from about 80 parts to about 92 parts of nitrile based on 100 parts of the nitrile/chloroprene blend.

Regardless of the particular structure of the nitrile rubber and polychloroprene rubber blend that can be used in one or more layers of the elastomeric article of the present invention, various additional components, such as but not limited to an alkali agent, a metal oxide, a crosslinker, pigment, a defoamer, and a surfactant, can be incorporated during the compounding of the blended nitrile rubber and polychloroprene rubber formulation so that the overall glove can have certain desired properties. Conventional nitrile rubber medical exam gloves further require sulfur and/or an accelerator (e.g., a single dithiocarbamate accelerator, zincediethyldithiocarbamate (ZDEC), zinc mercaptobenzothiazole (ZMBT), diphenyl guanidine (DPG), or a combination thereof) to be present during the compounding of the nitrile rubber formulation to covalently link so that certain desired properties can be achieved. However, as will be discussed in further detail below, the present inventors have found that the blend of polychloroprene rubber with nitrile rubber requires no sulfur and/or vulcanization accelerators to form an elastomeric article having the same or improved desired qualities.

For instance, an alkali agent can be added to the nitrile rubber formulation to adjust the pH of the nitrile rubber formulation. Any suitable alkali agent can be used, and, in some embodiments, the alkali agent can be potassium hydroxide, ammonium hydroxide, or a combination thereof. In any event, the alkali agent can be used to adjust the nitrile rubber formulation to a pH that can range from about 9 to about 11, such as from about 9.2 to about 10.5, such as from about 9.5 to about 10.2. In addition to acting as a pH adjuster, the alkali agent can be utilized in combination with a metal oxide as discussed below to facilitate the formation of a nitrile rubber formulation that has high strength. Specifically, the alkali agent can include monovalent ions, such as K, Na, or H, which, although they do not have sufficient electron capacity to accommodate a bond with a second methylacrylic acid unit, may allow for weaker forms of associative bonding. As such, the alkali agents (e.g., monovalent salts) that can be used to increase the pH of the nitrile rubber formulation may also swell the nitrile rubber particles, making more carboxylic acid groups accessible to other crosslinking agents, such as the metal oxides discussed in more detail below. The positive charge of the cation can well balance the negative electrons of the acidic carboxyl groups.

Regardless of the particular alkali agent utilized, the alkali agent can be present in the compounded blended nitrile rubber and polychloroprene rubber formulation in an amount ranging from about 1.0 parts to about 2 parts, such as from about 1.1 parts to about 1.9 parts, such as from about 1.2 parts to about 1.6 parts, based on 100 dry parts of the blended rubber.

Further, the blended nitrile rubber and polychloroprene rubber formulation that can be used in one or more layers of the elastomeric article of the present invention can be chemically crosslinked to enhance the elasticity, strength, and chemical resistance of the nitrile rubber formulation. Conventionally, crosslinking of nitrile rubber can be accomplished in at least two ways: the butadiene subunits can be covalently crosslinked with sulfur and accelerators, while the carboxylated (organic acid) sites can be ionically crosslinked with metal oxides or salts. Ionic crosslinks, resulting from, for example, the addition of a metal oxide, such as zinc oxide, to the nitrile rubber formulation, can result in a nitrile rubber formulation having high tensile strength, puncture resistance, and abrasion resistance, as well as high elastic modulus (a measure of the force required to stretch a film of the rubber). The polychloroprene polymers can be crosslinked by the addition of a metal oxide, such as zinc oxide, to the formulation. The present inventors have found that the blended nitrile rubber and polychloroprene rubber formulation can be successfully covalently and ionically crosslinked with metal oxides or salts, including a trivalent metal oxide crosslinker, without the addition of sulfur and/or accelerators as compared to a conventional nitrile rubber article.

Including one or more metal oxides oxide crosslinkers in the blended nitrile rubber and polychloroprene rubber formulation can improve the dipping qualities and cure rates of the formulation for crosslinking of the polymers. In contrast, when one or more metal oxides such as zinc oxide are not employed, the curing time required to reach an optimum state of cure can be much longer and the curing may be less efficient. This means that the crosslinks are longer and there may be a higher amount of crosslinker that does not crosslink polymer chains. The result, if metal oxides are omitted, can be a less-effectively cured rubber that has lowered heat resistance and less chemical resistance.

While not intending to be bound by theory, it is believed that the matrix structure and strength of the nitrile rubber formulation that can be used in one or more layers of the glove of the present invention may result from the interaction of all ions present in the system, in particular, divalent or higher valence cations, with the carboxylic acid components of the polymer matrix. Divalent or multivalent cations, such as Mg, Ca, Zn, Cu, Ti, Cd, Al, Fe, Co, Cr, Mn, and Pb, can crosslink with the carboxyl groups of the ionized carboxylic acids, forming relatively stable bonds. Of these cation species, Mg, Ca, Zn, Cu, or Cd are more desirable. Preferably, the methylacrylic acid monomers are located relatively close to each other in the polymer matrix structure; in such a fashion, the divalent or multivalent cation can crosslink with two or more nearby acid units. The positive charge of the cation can well balance the negative electrons of the acidic carboxyl groups. It is believed that, absent divalent or multivalent cations, multiple polymer chains in the nitrile emulsions are not well crosslinked together.

Regardless of the particular metal oxide utilized, the metal oxide can be present in the compounded blended rubber formulation in an amount ranging from about 0.1 parts to about 1.5 parts, such as from about 0.2 parts to about 1.25 parts, such as from about 0.3 parts to about 1.0 parts, based on 100 dry parts of the blended rubber.

Moreover, a crosslinker such as a trivalent metal oxide compound can be present to contribute to the crosslinking of the carboxylated nitrile butadiene subunits and the polychloroprene. The crosslinker crosslinks with nitrile polymer chains at multiple sites and forms covalent bonds with the carboxyl groups. Crosslinking at multiple sites improves the durability of the elastomeric article and results in greater elongation. The crosslinker can be present in the compounded blended rubber formulation in an amount ranging from about 0.3 parts to about 2.0 parts, such as from about 0.5 parts to about 1.5 parts, such as from about 0.8 parts to about 1.2 parts, based on 100 dry parts of the blended rubber.

Moreover, the blended rubber formulation of the present invention can include one or more of a titanium dioxide or similar filler, a color pigment, or a combination thereof to provide a desired level of color, contrast, brightness, saturation, value, and/or opaqueness. Specifically, the compounded nitrile rubber formulation can include titanium dioxide or any other similar filler in an amount ranging from about 0.25 parts to about 5 parts, such as from about 1 parts to 3 parts, such as from about 1.1 parts to about 1.5 parts, based on 100 dry parts of the blended rubber. Without intending to be limited by any particular theory, the present inventors have found that the inclusion of titanium dioxide or any other similar filler in such amounts can prevent the bleed through of a color pigments between various layers of the glove in a multi-layer glove. Further, the compounded nitrile rubber formulation can include a lighter colored pigment (e.g., red, orange, yellow, green, blue, indigo, violet, or a combination thereof) or a darker colored pigment (e.g., black, brown, dark gray, blue, purple, etc.) in an amount ranging from about 0.25 parts to about 3 parts, such as from about 0.5 parts to about 2 parts, such as from about 0.6 parts to 1 part, based on 100 dry parts of the blended rubber. One example of a green pigment may be a MaxFSet Green GG. Moreover, the present inventors have discovered that the ratio of the parts of titanium dioxide to the colored pigment in the blended rubber formulation can be controlled to achieve a glove layer having desired saturation (color purity) and value (lightness or darkness) percentages. Specifically, the ratio of parts of titanium dioxide to the parts of colored pigment in the nitrile rubber formulation can range from about 0.25 parts to about 20 parts titanium dioxide per parts of colored pigment, such as from about 0.5 parts to about 10 parts titanium dioxide per part of colored pigment, such as from about 1 part to about 5 parts titanium dioxide per part of colored pigment.

Further, the blended rubber formulation may include a defoamer. The defoamer can prevent and/or break bubbles in the blended rubber formulation emulsion. As a result, the use of a defoamer in the blended rubber formulation can give substantial freedom from defects such as fisheyes and surface imperfections during formation of the blended rubber film on the mold or former. In some embodiments, the defoamer may be an emulsifiable, Silica-type, oil based defoamer and an anti-webbing agent. In some embodiments, the defoamer may be present in an amount ranging from about 0 parts to about 0.5 parts based on 100 dry parts of the blended rubber, such as from about 0.005 to about 0.1 parts based on 100 dry parts of the blended rubber, such as from about 0.01 to about 0.05 parts based on 100 dry parts of the blended rubber.

Regardless of the specific components utilized to form the blended rubber formulation of the present invention, after compounding, the resulting blended rubber formulation can have an as-received total solids content (TSC) of about 40-45%. The blended rubber solids content of the emulsion can be diluted to form a bath of blended rubber emulsion that is suitable for forming the glove to be coated on the former to create a bath having rubber solids content to form a glove of the desired thickness. The blended rubber solids content of the bath can have a TSC ranging from about 15% to about 30%, such as from about 17.5% to about 27.5%, such as from about 20% to about 25%. The reduction of the TSC by dilution enables for the manufacture of single- or multi-layered elastomeric articles. Further, it is to be understood that the components of the blended rubber formulation can be compounded by adding them to the blended rubber formulation in any order.

After the blended rubber formulation is compounded, the formulation can be used to form one or more layers of any suitable elastomeric article. In one particular embodiment, the blended rubber formulation can be used to form a glove having improved softness and flexibility as compared to traditional medical exam gloves, as discussed in more detail below.

Coagulant Solution

After the blended rubber formulation is compounded, the formulation can be used in a coagulant dip-coating process to form an elastomeric article such as an elastomeric glove. In this process, a mold or "former" is dipped into an aqueous coagulant solution prior to dipping the former into the nitrile rubber formulation to cause gelation of the nitrile rubber over the mold or former surface. The coagulant solution comprises a powder free coagulant that includes one or more metallic salts as a coagulating agent (e.g., nitrate, sulfate, or chloride salts of calcium, aluminum, or zinc, or a combination thereof). In one embodiment, the coagulating agent may be calcium nitrate. The metallic salts can be present in the solution in an amount ranging from about 5 wt % to about 20 wt %, such as from about 7.5 wt % to about 17.5 wt %, such as from about 10 wt % to about 15 wt % based on the total weight of the solution. The metallic salt, e.g. calcium nitrate, in the coagulant formulation is the source for ions that trigger subsequent coagulation.

In addition to a powder free coagulant, the solution can include one or more other components. For instance, the solution can include a wax, a release agent, a hydrogel, a silicone, a gel, an antimicrobial agent (e.g., silver (Ag++), copper (Cu++), polyhexamethylene biguanide (PHMB), etc.), an acrylic polymer, a peroxide crosslinking agent, an emollient (e.g., shea butter, petroleum, etc.), a hydrophilic agent, a hydrophobic agent, a colorant, a dye, a polyolefin-based powder (e.g., a polyethylene powder or a polypropylene powder), a surfactant, a soap, an acidic agent, an alkali agent, a defoamer, or a combination thereof. These additional components can be present in the solution in a cumulative amount ranging from about 0.1 wt % to about 30 wt %, such as from about 0.5 wt % to about 25 wt %, such as from about 1 wt % to about 20 wt % based on the total weight of the solution.

A surfactant can be included in the coagulant solution to provide enhanced wetting to and of the former. The enhanced wetting of the former is particularly useful with respect to an elastomeric article made by multiple dips of the former into the blended rubber emulsion.

A defoamer can be included in the coagulant solution to prevent bubbles in the coagulant solution. The defoamer may be an oil-based defoamer and anti-webbing agent that promotes wetting of other low energy substrates, such as plastics and contaminated or improperly cleaned surfaces.

The defoamer may be present in the coagulant solution in an amount ranging from about 0.001 wt % to about 1 wt %, such as from about 0.002 wt % to about 0.75 wt %, such as from about 0.003 wt % to about 0.5 wt %.

According to the present invention, the coagulant solution can include a release agent. The release agent is in the form of a "waxy" material and is used in the fabrication of a powder-free dipped article. The release agent can be an anti-tack agent that is a rubber lubricant mixed into the coagulant solution to aid in preventing the coagulated nitrile rubber article from sticking to the mold or former. The release agent is typically a low-melting organic mixture or compound of high molecular weight, solid at room temperature and generally similar to fats and oils except that it contains no glycerides. For example, the release agent can be: an inorganic powder (e.g., carbonates, stearates, oxides, hydroxides, aluminates, etc.); a petroleum wax with a melting point of less than about 200° C. (e.g., melting point between about 135° C. to about 180° C.) which can be in the form of paraffin waxes, microcrystalline waxes, or petroleum jelly; a natural animal or insect wax such as bee's wax; or a synthetic wax (e.g., polyethylene waxes). Generally speaking, the release agent can be emulsified in the coagulant solution and can be present in an amount ranging from about 0.1 wt % to about 10 wt %, such as from about 0.5 wt % to about 7.5 wt %, such as from about 1 wt % to about 5 wt %, such as about 2.5 wt %. The release agent can aid in the subsequent release of the completed elastomeric article from the former with minimal to no loose particulates.

A combination of release agents may be used in the coagulant solution. For example, the release agent may be a salt or ester of stearic acid, for example having the formula $Ca(O_2C_{18}H_{35})_2$ or calcium stearate. Calcium stearate may be in the form of a water-based polymer lubricant dispersion such as Nobel 7001. Another example of a release agent is an inorganic powder, for example calcium carbonate. In one particular embodiment, both calcium stearate and calcium carbonate may be used as release agents in the coagulant solution. The ratio of calcium carbonate to calcium stearate present in the coagulant solution may range from about 1:5 to about 1:15, such as from about 1:7.5 to about 1:12.5, for example about 1:10. The calcium carbonate may be present in an amount ranging from 0.05 wt % to about 5 wt %, such as from about 0.1 wt % to about 2.5 wt %, such as about 0.15 wt % to about 1 wt %. The calcium stearate may be present in an amount ranging from about 0.1 wt % to about 10 wt %, such as from about 0.5 wt % to about 7.5 wt %, such as from about 1 wt % to about 5 wt %, such as about 2 wt %.

A remainder of the coagulant solution may be made up of water. Water may be present in the coagulant solution in an amount ranging from 70 wt % to 92 wt %, such as from 75 wt % to 90 wt %, such as from 80 wt % to 88 wt %.

Glove Formation

Figure 2:
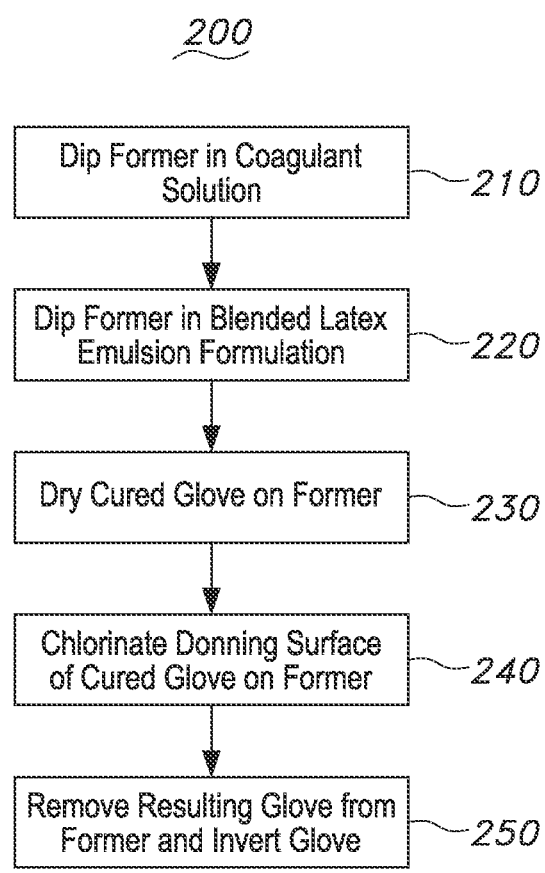
FIG. 2 illustrates a method of forming the elastomeric glove of FIG. 1 according to the present invention.

The method steps of formation of an elastomeric article of the present invention, in which the article is a glove, are shown generally in the flow chart of FIG. 2. The process for forming an elastomeric glove entails providing a clean hand-shaped mold, also known as a "former". The former may be made from any suitable material that can be heated to a temperature of at least 130° C., such as ceramics and synthetic materials. For example, in one embodiment the former may be made of porcelain. The surface of the former defines the exterior or grip surface of the completed glove.

The former is conveyed on a central chain or conveyer belt through a preheated oven to evaporate any water present. The former may be preheated to a temperature ranging from approximately 55° C. to 60° C., for example about 58° C. At step 210, the former is then dipped into an aqueous coagulant solution prepared in accordance with the above description of the coagulant solution. The dip time for the solution can range from less than about 2 seconds to up to about 60 seconds. In one particular embodiment, a dip time between about 3 seconds and 10 seconds is desirable. For instance, the dip time can be about 5 seconds. The residual heat in the preheated former from the oven evaporates the water in the coagulant solution and leaves the former relatively uniformly coated with the residuals (i.e. at least the coagulant ions and the release agent).

In step 220, the coated former is then dipped into a bath of compounded nitrile rubber/chloroprene rubber blend, which may be pigmented. The composition of the bath of pigmented compounded nitrile rubber/chloroprene rubber blend is prepared in accordance with the above description of the blended nitrile rubber/chloroprene rubber formulation. In one embodiment, the color pigment of the nitrile rubber formulation may be green such that the compounded nitrile rubber/chloroprene rubber is a green pigmented compounded nitrile rubber/chloroprene rubber blend.

During the dipping process, the coagulating agent, for example calcium ions, on the former causes the rubber blend to coalesce into a relatively uniform layer about the former, thus covering the coagulant formulation. The former is then withdrawn from the bath and the coagulated layer of rubber blend is permitted to fully coalesce. During the dipping process, the glove former is dipped in the nitrile rubber emulsion for a dwell time duration ranging from about 5 seconds up to about 60 seconds. Desirably, in a single-dip process, the dwell time of the dip may be between about 7 seconds and 12 seconds. In one embodiment, the dwell time may be between about 7 to 10 seconds. Only one dip may be necessary to attain the desired glove thickness in the palm area. However, multiple dips are possible, for example to thicken the rubber layer. In the case of a multiple-dip process, the dwell time of each of the dips may each be shorter than the dwell time of a single dip process.

During the aforementioned dip processes, faster entry and exit speeds of the glove former into the blended rubber formulation dipping solution can provide a more even thickness profile to the glove, due at least in part to the reduced difference in residence time of the fingertip and cuff areas of the formers in the compounded formulations. The former can be extracted from the dip bath at or near an initial vertical position and raised such that the finger tips are elevated to a horizontal or greater than horizontal position (e.g., tilted to an angle of about 20° to 45° above horizontal) for a brief period of time ranging from a few seconds to about 40 seconds. Quickly thereafter, the fingertips can be lowered to a position or angle between horizontal and initial vertical, while rolling the former along its longitudinal axis. The raising and lowering action can be repeated in a sinusoidal or wave-like motion. This process can enable the elastomeric material formulations (e.g., the blended rubber formulations) to distribute more evenly over the mold or former and produce a substrate product that is thinner overall.

After the step of dipping and removing the former from the blended rubber bath and the coalescence of the blended rubber layer, the former with the pigmented nitrile/polychloroprene gel is then dipped into a leaching tank. In the leaching tank, hot water is circulated to remove water-soluble components, such as residual coagulant metallic salts (e.g. calcium nitrates) and other leachable material. The leaching process may take about 3 minutes to about 10 minutes at a water temperature ranging from about 49° C. to about 66° C. (about 120-150° F.).

At step 230, the former with pigmented rubber blend is then conveyed into an oven so that the pigmented nitrile/polychloroprene gel is dried and cured at a temperature of about 100° C. to about 110° C. to evaporate any excess moisture from the surface of the formed glove.

The glove is then subjected to processing. During processing of the rubber glove according to the present invention, while the glove remains on the glove former, one side of the glove is subjected to halogenations (i.e., chlorination) in step 240. That is, the glove will have a chlorinated first surface forming a donning side of the glove once removed from the former. The former and glove are dipped in a sodium hypochlorite solution having a concentration ranging from about 1.5 wt % to about 4.5 wt %, such as from about 1.75 wt % to about 4.25 wt %, such as from about 2 wt % to about 4 wt %. The former and glove are then transferred from the sodium hypochlorite solution to a tank containing hydrochloric acid having a concentration ranging from about 0.1 wt % to about 1.5 wt %, such as from about 0.15 wt % to about 1.25 wt %, such as from about 0.2 wt % to about 1 wt %. In the tank of hydrochloric acid, a reaction takes place to generate hypochlorous acid on the surface of the glove. This process reduces the tackiness of the surface of the glove and causes the surface of the formed glove to become more slick. The next step is to rinse off excess chemicals from the chlorination process by dipping the former with the chlorinated glove into a series of 3 to 4 tanks of heated water. Each of the tanks of heated water may have a temperature ranging from about 85° C. to about 95° C., such as from about 87.5° C. to about 92.5° C., such as from about 89° C. to about 91° C. After the step of rinsing, the former with the chlorinated glove is transferred into a tunnel of ovens having a temperature ranging from about 70° C. to about 150° C., such as from about 80° C. to about 140° C., such as from about 90° C. to about 130° C., for another step of drying and curing the chlorinated glove. The drying and curing step of the chlorinated glove may last for about 30 minutes.

Next, the former with the cured, chlorinated glove is transferred to a stripping station. At the stripping station, in step 250, the glove is removed from the former and inverted to turn the glove inside out. By inverting the glove, the chlorinated surface of the glove becomes the inside of the glove and functions as an exemplary donning layer 120.

Upon formation and stripping of a plurality of gloves, the gloves may be packed into dispensers according to a required or desired quantity per dispenser. For example, 100 gloves may be packed into a dispenser or box.

Examples

Elastomeric articles were made using a nitrile/chloroprene rubber blended formulation using the process described above, and then subjected to mechanical testing. The formulation of the blended nitrile/chloroprene latex dispersion is shown in Table 1, with amounts represented in parts per hundred rubber (phr). Mechanical properties of the gloves were tested both before and after aging at 80° C.+/−2° C. for 0 days, 9 days, 25 days and 41 days. The tensile testing parameters and methods are defined in American Society for Testing and Materials (ASTM) test standard D-412-98a. In the present invention, the ASTM protocol was employed with no changes. The testing apparatus used was an Intron® tonometer, model 5564, with a static load cell of capacity about +/−100 N, and a XL extensometer. However, it is to be understood that other similar kinds of equipment could be used, as long as the machine met the requirements of the ASTM standard.

TABLE 1

Formulation

| Component | Formulation (phr.) |
| --- | --- |
| Nitrile latex | 89-91 |
| Chloroprene latex | 9-11 |
| KOH | 1.2-1.6 |
| Crosslinker | 0.8-1.2 |
| ZnO | 0.3-0.7 |
| Surfactant | 0.1-0.3 |
| $TiO_2$ | 1.1-1.5 |
| Pigment | 0.6-0.7 |
| Antioxidant | 0.3-0.7 |
| Defoaming | 0-0.02 |

TABLE 2

Material Properties

| Aging condition | 100% Modulus (MPa) | 300% Modulus (MPa) | 500% Modulus (MPa) | Tensile strength (MPa) | Force at break (N) | Elongation at break (%) |
| --- | --- | --- | --- | --- | --- | --- |
| Zero Time | 2.86 | 5.70 | 18.48 | 31.10 | 6.64 | 573 |
| 80° C. for 9 days | 2.74 | 5.27 | 15.96 | 36.19 | 7.31 | 606 |
| 80° C. for 25 days | 3.03 | 5.90 | 17.75 | 40.11 | 7.99 | 605 |
| 80° C. for 41 days | 3.58 | 6.29 | 17.12 | 42.46 | 8.58 | 629 |

Additionally, the material properties of a comparative nitrile glove are shown in Table 3. The comparative nitrile glove is a Halyard® STERLING® nitrile medical exam glove (a nitrile-butadiene rubber glove) which had an average palm thickness of about 0.08 mm. Mechanical properties of the gloves were tested both before and after aging at 100° C.+/−2° C. for 0 days, 3 days, 5 days and 11 days. The tensile testing parameters and methods are defined in American Society for Testing and Materials (ASTM) test standard D-412-98a. In the present invention, the ASTM protocol was employed with no changes. The testing apparatus used was an Intron® tonometer, model 5564, with a static load cell of capacity about +/−100 N, and a XL extensometer. However, it is to be understood that other similar kinds of equipment could be used, as long as the machine met the requirements of the ASTM standard

TABLE 3

Material Properties of Comparative Nitrile Glove

| Aging condition | 100% Modulus (MPa) | 300% Modulus (MPa) | 500% Modulus (MPa) | Tensile strength (MPa) | Force at break (N) | Elongation at break (%) |
| --- | --- | --- | --- | --- | --- | --- |
| Zero Time | 3.49 | 7.11 | 21.83 | 37.02 | 7.38 | 573 |
| 100° C. for 3 days | 3.45 | 6.89 | 20.84 | 39.96 | 8.10 | 578 |
| 100° C. for 5 days | 4.07 | 9.16 | 31.39 | 41.75 | 8.38 | 539 |
| 100° C. for 11 days | 4.05 | 9.08 | 33.21 | 42.26 | 8.47 | 532 |

As shown in Tables 2 and 3 above, the elastomeric article of the present invention had approximately the same elongation at break (%) as the comparative nitrile glove prior to aging of the glove. However, the elastomeric article of the present invention gained elasticity over time, as shown by the elongation at break (%) increasing as the article was aged to 9 days and up to 41 days. In contrast, the comparative nitrile glove lost some elasticity as the glove was aged, with the elongation at break (%) decreasing from 573 at 0 days to 532 at 11 days. Without intending to be limited by any particular theory, the present inventors have found that the elastomeric article formed by a blend of nitrile rubber and polychloroprene rubber and crosslinked with a trivalent compound crosslinker can have improved durability and higher elongation compared to other elastomeric articles, such as the comparative nitrile glove described above.

Additionally, the present inventors have found that the elastomeric article of the present invention has superior handfeel compared to the conventional nitrile medical exam glove. Specifically, the elastomeric article of the present invention has improved softness in comparison to the conventional nitrile medical exam glove. As a result, gloves or other elastomeric articles formed from the elastomeric material of the present invention may be easier to don and more comfortable to wear, especially for longer periods of time, than conventional nitrile medical exam gloves, thereby making gloves according to the present invention more desirable to a user. The improved softness and comfort of the gloves of the present invention may further improve users' compliance and adherence to glove-wearing standards in clinical settings.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. An elastomeric article comprising: an article comprising a flexible layer of elastomeric material, wherein the elastomeric material is formed from a blended emulsion of nitrile rubber and chloroprene rubber, the article having a first surface and a second surface,
    wherein the blended emulsion comprises a divalent metal oxide and a trivalent crosslinker, and
    wherein the blended emulsion is free from sulfur and free from a dithiocarbamate accelerator, zincediethyldithiocarbamate (ZDEC), zinc mercaptobenzothiazole (ZMBT), diphenyl guanidine (DPG), or a combination thereof.
2. The elastomeric article of claim 1, wherein the ratio of nitrile rubber to chloroprene rubber in the blended emulsion is in a range from about 50:50 to about 95:5.
3. The elastomeric article of claim 1, wherein the blended emulsion includes a solids content of between about 15 percent and about 30 percent, by weight.
4. The elastomeric article of claim 1, wherein coagulation of the blended emulsion to form the elastomeric article is accelerated by the crosslinker.
5. The elastomeric article of claim 1, wherein the article is a glove.
6. The elastomeric article of claim 5, wherein the first surface is a donning side of the glove and the second surface is a grip side of the glove.
7. The elastomeric article of claim 1, wherein coagulation of the blended emulsion to form the elastomeric article is accelerated by a metallic salt, wherein the metallic salt includes nitrate, sulfate, or chloride salts of calcium, aluminum, or zinc, or a combination thereof.
8. The elastomeric article of claim 7, wherein coagulation of the blended emulsion to form the elastomeric article is further accelerated by the trivalent crosslinker.
9. The elastomeric article of claim 8, wherein the metallic salt is a divalent compound.
10. The elastomeric article of claim 8, wherein the metallic salt is calcium nitrate.
11. The elastomeric article of claim 8, wherein the trivalent crosslinker is a metallic oxide that forms bonds with carboxyl groups of the nitrile rubber.

* * * * *